(12) United States Patent
Bizios et al.

(10) Patent No.: US 9,357,911 B2
(45) Date of Patent: Jun. 7, 2016

(54) INTEGRATION AND FUSION OF DATA FROM DIAGNOSTIC MEASUREMENTS FOR GLAUCOMA DETECTION AND PROGRESSION ANALYSIS

(75) Inventors: Dimitrios Bizios, Malmö (SE); Boel Bengtsson, Trelleborg (SE); Anders Heijl, Lund (SE)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 13/467,907

(22) Filed: May 9, 2012

(65) Prior Publication Data

US 2012/0287401 A1 Nov. 15, 2012

Related U.S. Application Data

(60) Provisional application No. 61/484,149, filed on May 9, 2011.

(51) Int. Cl.
*A61B 3/14* (2006.01)
*A61B 3/00* (2006.01)
*A61B 3/10* (2006.01)

(52) U.S. Cl.
CPC .............. *A61B 3/0025* (2013.01); *A61B 3/102* (2013.01)

(58) Field of Classification Search
CPC ............ A61B 3/14; A61B 3/12; A61B 3/102; A61B 3/0025; A61B 3/10; A61B 3/113; A61B 3/107; A61B 3/1005; A61B 5/0066; A61B 3/00; A61B 3/0041; A61B 3/1225; A61B 3/145; A61B 3/0091; A61B 3/032; A61B 3/1025; A61B 3/028; A61B 3/036
USPC ........... 351/205, 206, 246; 382/131; 600/437, 600/438, 439
See application file for complete search history.

(56) References Cited

U.S. PATENT DOCUMENTS 5,381,195 A 1/1995 Rootzen et al.
5,461,435 A 10/1995 Rootzen et al.
(Continued)

FOREIGN PATENT DOCUMENTS

EP 1666009 A2 6/2006
JP 9-313447 A 12/1997
(Continued)

OTHER PUBLICATIONS

Bowd et al, Bayesian machine learning classifiers for combining structural and functional measurements to classify healthy and glaucomatous eyes, Invest Ophthalmol Vis Sci. Mar. 2008;49(3):p. 945-953.*

(Continued)

*Primary Examiner* — James Greece
*Assistant Examiner* — Sharrief Broome
(74) *Attorney, Agent, or Firm* — Morrison & Foerster LLP (57) ABSTRACT

Systems and methods for improving the reliability of glaucoma diagnosis and progression analysis are described. The measurements made from one type of diagnostic device are adjusted based on another measurement using a priori knowledge of the relationship between the two measurements including the relationship between structure and function, knowledge of disease progression, and knowledge of instrument performance at specific locations in the eye. The adjusted or fused measurement values can be displayed to the clinician, compared to normative data, or used as input in a machine learning classifier to enhance the diagnostic and progression analysis of the disease.

29 Claims, 4 Drawing Sheets

(56) References Cited

U.S. PATENT DOCUMENTS

| | | | |
|---|---|---|---|
| 5,598,235 A | 1/1997 | Heijl et al. | |
| 5,878,746 A | 3/1999 | Lemelson et al. | |
| 6,068,377 A | 5/2000 | McKinnon et al. | |
| 6,247,812 B1 | 6/2001 | Miehle et al. | |
| 6,293,674 B1 | 9/2001 | Huang et al. | |
| 6,735,331 B1 | 5/2004 | Binnun et al. | |
| 7,166,079 B2 | 1/2007 | Febbroriello et al. | |
| 7,237,898 B1 | 7/2007 | Hohla et al. | |
| 7,306,560 B2 | 12/2007 | Iliff | |
| 7,392,199 B2 | 6/2008 | Karlov et al. | |
| 7,406,200 B1 | 7/2008 | Syeda-Mahmood et al. | |
| 7,458,936 B2 | 12/2008 | Zhou et al. | |
| 7,519,227 B1 | 4/2009 | Syeda-Mahmood et al. | |
| 8,132,916 B2 | 3/2012 | Johansson | |
| 2004/0105073 A1* | 6/2004 | Maddalena et al. | 351/205 |
| 2005/0094099 A1 | 5/2005 | Newman et al. | |
| 2006/0025658 A1 | 2/2006 | Newman et al. | |
| 2006/0084856 A1 | 4/2006 | Biggins et al. | |
| 2007/0038042 A1 | 2/2007 | Freeman et al. | |
| 2007/0197932 A1 | 8/2007 | Feke et al. | |
| 2008/0309881 A1 | 12/2008 | Huang et al. | |
| 2008/0312552 A1 | 12/2008 | Zhou et al. | |
| 2009/0073387 A1* | 3/2009 | Meyer et al. | 351/246 |
| 2009/0119021 A1 | 5/2009 | Schuett et al. | |
| 2009/0244485 A1* | 10/2009 | Walsh et al. | 351/221 |
| 2010/0238405 A1 | 9/2010 | Newman et al. | |
| 2010/0241450 A1* | 9/2010 | Gierhart et al. | 705/3 |
| 2010/0249532 A1* | 9/2010 | Maddess et al. | 600/300 |
| 2010/0277691 A1 | 11/2010 | Huang et al. | |
| 2010/0290005 A1 | 11/2010 | Huang et al. | |
| 2010/0290006 A1 | 11/2010 | Flanagan et al. | |
| 2011/0046480 A1 | 2/2011 | Yonezawa | |
| 2011/0190657 A1* | 8/2011 | Zhou et al. | 600/558 |

FOREIGN PATENT DOCUMENTS

| | | | | |
|---|---|---|---|---|
| JP | 2005-301816 A | | 10/2005 | |
| JP | 2005301816 A | * | 10/2005 | G06F 17/60 |
| JP | 2008-73188 A | | 4/2008 | |
| WO | 2007/098070 A2 | | 8/2007 | |
| WO | 2007/098070 A3 | | 6/2008 | |

OTHER PUBLICATIONS

Final Office Action received for U.S. Appl. No. 12/157,850, mailed on Sep. 23, 2013, 15 pages.
Final Office Action received for U.S. Appl. No. 12/849,686, mailed on Oct. 11, 2013, 12 pages.
Non-Final Office Action received for U.S. Appl. No. 12/157,850, mailed on Dec. 20, 2013, 14 pages.
Non-Final Office Action received for U.S. Appl. No. 12/849,686, mailed on Apr. 21, 2014, 11 pages.
Office Action Received for Japanese Patent Application No. 2012-524139, mailed on Mar. 4, 2014, 8 pages (4 pages of English Translation and 4 pages of Official Copy).
"Humphrey® Glaucoma Progression Analysis (GPA) Software", Carl Zeiss Meditec, Inc., 2003, 8 pages.
Invitation to Pay Additional Fees received for PCT Patent Application No. PCT/EP2010/004846, mailed on Jan. 13, 2011, 6 pages.
International Search Report and Written Opinion received for PCT Patent Application No. PCT/EP2010/004846, mailed on Mar. 28, 2011, 18 pages.
Final Office Action received for U.S. Appl. No. 12/157,850 mailed on Oct. 12, 2012, 13 pages.
Non Final Office Action received for U.S. Appl. No. 12/157,850, mailed on Mar. 28, 2013, 14 pages.
Non Final Office Action received for U.S. Appl. No. 12/157,850, mailed on Sep. 29, 2011, 14 pages.
Non Final Office Action received for U.S. Appl. No. 12/849,686, mailed on Mar. 14, 2013, 10 pages.
Agarwal et al., "Target Intraocular Pressure in Glaucoma Management", Asian Journal of Ophthalmology, vol. 3, No. 3,4, 2001, pp. 15-18.
Anderson et al., "Encounters in Glaucoma Research 3, How to Ascertain Progression and Outcome", Kugler Publications BV, 1996, pp. 184-186.
Artes et al., "Longitudinal Changes in the Visual Field and Optic Disc in Glaucoma", Progress in Retinal and Eye Research, vol. 24, 2005, pp. 333-354.
Bengtsson et al., "A Visual Field Index for Calculation of Glaucoma Rate of Progression", American Journal of Ophthalmology, vol. 145, No. 2, Feb. 2008, pp. 343-353.
Brusini et al., "Staging Functional Damage in Glaucoma: Review of Different Classification Methods", Survey of Ophthalmology, vol. 52, No. 2, Mar.-Apr. 2007, pp. 156-179.
Chauhan et al., "Optic Disc and Visual Field Changes in a Prospective Longitudinal Study of Patients With Glaucoma: Comparison of Scanning Laser Tomography With Conventional Perimetry and Optic Disc Photography", Arch Ophthalmology, vol. 119, 2001, pp. 1492-1499.
Chauhan et al., "Technique for Detecting Serial Topographic Changes in the Optic Disc and Peripapillary Retina Using Scanning Laser Tomography", Investigative Ophthalmology & Visual Science, vol. 41, No. 3, Mar. 2000, pp. 775-782.
Chauhan, Balwantray C., "Detection of Glaucomatous Changes in the Optic Disc", Heidelberg Engineering, On-line publication, Dec. 2005, pp. 53-65.
Delgado et al., "Automated Perimetry: A Report by the American Academy of Ophthalmology", American Academy of Ophthalmology, vol. 109, No. 12, Dec. 2002, pp. 2362-2374.
Fortune et al., "Retinal Nerve Fiber Layer Birefringence Declines Prior to Thickness After Onset of Experimental Glaucoma or Optic Nerve Transection in Non-Human Primates", Investigative Ophthalmology & Visual Science, Suppl., 49, Abstract No. 3761, 2008, 1 page.
Gotzinger et al., "Retinal Nerve Fiber Layer Birefringence of Healthy and Glaucomatous Eyes Measured with Polarization Sensitive Spectral Domain OCT", Investigative Ophthalmology & Visual Science, Suppl., 49, abstract No. 3762, 2008, 1 page.
Harwerth et al., "Neural Losses Correlated with Visual Losses in Clinical Perimetry", Investigative Ophthalmology & Visual Science, vol. 45, No. 9, Sep. 2004, pp. 3152-3160.
Harwerth et al., "The Relationship between Nerve Fiber Layer and Perimetry Measurements", Investigative Ophthalmology & Visual Science, vol. 48, No. 2, Feb. 2007, pp. 763-773.
Harwerth et al., "Visual Field Defects and Retinal Ganglion Cell Losses in Patients With Glaucoma", Arch Ophthalmology, vol. 124, Jun. 2006, pp. 853-859.
Horn et al., "Correlation Between Local Glaucomatous Visual Field Defects and Loss of the Nerve Fiber Layer Thickness Measured with Polarimetry (GDx) and Spectral Domain OCT", Investigative Ophthalmology & Visual Science, Suppl., 49, Abstract No. 732, 2008, 1 page.
Huang et al., "Microtubules Contribute to the Birefringence of the Retinal Nerve Fiber Layer", Investigative Ophthalmology & Visual Science, vol. 46, No. 12, Dec. 2005, pp. 4588-4593.
Kanamori et al., "Regional Relationship Between Retinal Nerve Fiber Layer Thickness and Corresponding Visual Field Sensitivity in Glaucomatous Eyes", Arch Opthalmology, vol. 126, No. 11, Nov. 2008, pp. 1500-1506.
Kerrigan-Baumrind et al., "Number of Ganglion Cells in Glaucoma Eyes Compared with Threshold Visual Field Tests in the Same Persons", Investigative Ophthalmology & Visual Science, vol. 41, No. 3, Mar. 2000, pp. 741-748.
Lin et al., "Optic Nerve Head and Retinal Nerve Fiber Layer Analysis : A Report by the American Academy of Ophthalmology", Ophthalmology, vol. 114, No. 10, Oct. 2007, pp. 1937-1949.
Mardin et al., "Improving Glaucoma Diagnosis by the Combination of Perimetry and HRT Measurements", J. Glaucoma, vol. 15, No. 4, Aug. 2006, pp. 299-305.
Medeiros et al., "Comparison of the GDx VCC Scanning Laser Polarimeter, HRT II Confocal Scanning Laser Ophthalmoscope, and Stratus OCT Optical Coherence Tomograph for the Detection of Glaucoma", Arch Ophthalmolpgy, vol. 122, 2004, pp. 827-837.

(56) References Cited

OTHER PUBLICATIONS

Patterson et al., "A New Statistical Approach for Quantifying Change in Series of Retinal and Optic Nerve Head Topography Images", Investigative Ophthalmology & Visual Science, vol. 46, No. 5, May 2005, pp. 1659-1667.

Quigley et al., "Optic Nerve Damage in Human Glaucoma: III. Quantitative correlation of Nerve Fiber Loss and Visual Field Defect in Glaucoma, Ischemic Optic Neuropathy, Papilledema, and Toxic Neuropathy", Arch Ophthalmology, vol. 100, Jan. 1982, pp. 135-146.

Quigley et al., "Retinal Ganglion Cell Atrophy Correlated with Automated Perimetry in Human Eyes with Glaucoma", American Journal of Ophthalmology, vol. 107, No. 5, May 1989, pp. 453-464.

Reus et al., "Scanning Laser Polarimetry of the Retinal Nerve Fiber Layer in Perimetrically Unaffected Eyes of Glaucoma Patients", American Academy of Ophthalmology, vol. 111, No. 12, Dec. 2004, pp. 2199-2203.

Reus et al., "The Relationship Between Standard Automated Perimetry and GDx VCC Measurements", Investigative Ophthalmology & Visual Science, vol. 45, No. 3, Mar. 2004, pp. 840-845.

Shah et al., "Combining Structural and Functional Testing for Detection of Glaucoma", American Academy of Ophthalmology, vol. 113, No. 9, Sep. 2006, pp. 1593-1602.

Strouthidis et al., "Structure and Function in Glaucoma: The relationship between a Functional Visual Field Map and an Anatomic Retinal Map", Investigative Ophthalmology & Visual Science, vol. 47, No. 12, Dec. 2006, pp. 5356-5362.

Swanson et al., "Perimetric Defects and Ganglion Cell Damage: Interpreting Linear Relations Using a Two-Stage Neural Model", Investigative Ophthalmology & Visual Science, vol. 45, No. 2, Feb. 2004, pp. 466-472.

Vermeer et al., "Modeling of Scanning Laser Polarimetry Images of the Human Retina for Progression Detection of Glaucoma", IEEE Transactions on Medical Imaging, vol. 25, No. 5, May 2006, pp. 517-528.

Zhou et al., "Progress Analysis Algorithms for GDx VCC Retinal Nerve Fiber Layer Measurements", Arvo Abstract, 2006, 1 page.

Zhu et al., "Combining Structural and Functional Measurements to Improve Reproducibility of Follow Up Data in Glaucoma", Investigative Ophthalmology & Visual Science, Abstract No. 2572, 2009, 1 page.

Ajtony et al., "Relationship Between Visual Field Sensitivity and Retinal Nerve Fiber Layer Thickness as Measured by Optical Coherence Tomography", Investigative Ophthalmology & Visual Science, vol. 48, No. 1, Jan. 2007, pp. 258-263.

Arthur et al., "Agreement in Assessing Cup-to-Disc Ratio Measurement Among Stereoscopic Optic Nerve Head Photographs, HRT II, and Stratus OCT", J Glaucoma, vol. 15, No. 3, Jun. 2006, pp. 183-189.

Asman et al., "Glaucoma Hemifield Test: Automated Visual Field Evaluation", Archives of Ophthalmology, vol. 110, Jun. 1992, pp. 812-819.

Bengtsson et al., "A New Generation of Algorithms for Computerized Threshold Perimetry, SITA", Acta Ophthalmologica Scandinavica, vol. 75, 1997, pp. 368-375.

Bengtsson et al., "Effects of Input Data on the Performance of a Neural Network in Distinguishing Normal and Glaucomatous Visual Fields", Investigative Ophthalmology & Visual Science, vol. 46, No. 10, Oct. 2005, pp. 3730-3736.

Bizios et al., "Integration and Fusion of Standard Automated Perimetry and Optical Coherence Tomography Data for Improved Automated Glaucoma Diagnostics", BMC Ophthalmology, vol. 11, No. 20, 2011, pp. 1-11.

Bizios et al., "Machine Learning Classifiers for Glaucoma Diagnosis based on Classification of Retinal Nerve Fibre Layer Thickness Parameters Measured by Stratus OCT", Acta Ophthalmologica, vol. 88, 2010, pp. 44-52.

Bizios et al., "Trained Artificial Neural Network for Glaucoma Diagnosis Using Visual Field Data: A Comparison With Conventional Algorithms", J Glaucoma, vol. 16, No. 1, 2007, pp. 20-28.

Boland et al., "Evaluation of a Combined Index of Optic Nerve Structure and Function for Glaucoma Diagnosis", Boland and Quigley BMC Ophthalmology, vol. 11, No. 6, 2011, pp. 1-12.

Bowd et al., "Bayesian Machine Learning Classifiers for Combining Structural and Functional Measurements to Classify Healthy and Glaucomatous Eyes", Investigative Ophthalmology & Visual Science, vol. 49, No. 3, Mar. 2008, pp. 945-953.

Bowd et al., "Comparing Neural Networks and Linear Discriminant Functions for Glaucoma Detection Using Confocal Scanning Laser Ophthalmoscopy of the Optic Disc", Investigative Ophthalmology & Visual Science, vol. 43, No. 11, Nov. 2002, pp. 3444-3454.

Bowd et al., "Machine Learning Classifiers in Glaucoma", Optometry and Vision Science, vol. 85, No. 6, Jun. 2008, pp. 396-405.

Budenz et al., "Reproducibility of Retinal Nerve Fiber Thickness Measurements Using the Stratus OCT in Normal and Glaucomatous Eyes", Investigative Ophthalmology & Visual Science, vol. 46, No. 7, Jul. 2005, pp. 2440-2443.

Budenz et al., "Sensitivity and Specificity of the StratusOCT for Perimetric Glaucoma", Ophthalmology, vol. 112, No. 1, Jan. 2005, pp. 3-9.

Burgansky-Eliash et al., "Optical Coherence Tomography Machine Learning Classifiers for Glaucoma Detection: A Preliminary Study", Investigative Ophthalmology & Visual Science, vol. 46, No. 11, Nov. 2005, pp. 4147-4152.

Chan et al., "Comparison of Machine Learning and Traditional Classifiers in Glaucoma Diagnosis", IEEE Transactions on Biomedical Engineering, vol. 49, No. 9, Sep. 2002, pp. 963-974.

Chang et al., "New Developments in Optical Coherence Tomography for Glaucoma", Current Opinion in Ophthalmology, vol. 19, 2008, pp. 127-135.

Choma et al., "Sensitivity Advantage of Swept Source and Fourier Domain Optical Coherence Tomography", Optics Express, vol. 11, No. 18, Sep. 8, 2003, pp. 2183-2189.

Danesh-Meyer et al., "Relationship between Retinal Nerve Fiber Layer and Visual Field Sensitivity as Measured by Optical Coherence Tomography in Chiasmal Compression", Investigative Ophthalmology & Visual Science, vol. 47, No. 11, Nov. 2006, pp. 4827-4835.

Delong et al., "Comparing the Areas under Two or More Correlated Receiver Operating Characteristic Curves: A Nonparametric Approach", Biometrics, vol. 44, No. 3, Sep. 1988, pp. 837-845.

El Beltagi et al., "Retinal Nerve Fiber Layer Thickness Measured with Optical Coherence Tomography is Related to Visual Function in Glaucomatous Eyes", Ophthalmology, vol. 110, No. 11, Nov. 2003, pp. 2185-2191.

Ferreras et al., "Mapping Standard Automated Perimetry to the Peripapillary Retinal Nerve Fiber Layer in Glaucoma", Investigative Ophthalmology & Visual Science, vol. 49, No. 7, Jul. 2008, pp. 3018-3025.

Gardiner et al., "Evaluation of the Structure-Function Relationship in Glaucoma", Investigative Ophthalmology & Visual Science, vol. 46, No. 10, Oct. 2005, pp. 3712-3717.

Garway-Heath et al., "Mapping the Visual Field to the Optic Disc in Normal Tension Glaucoma Eyes", Ophthalmology, vol. 107, No. 10, Oct. 2000, pp. 1809-1815.

Goldbaum et al., "Comparing Machine Learning Classifiers for Diagnosing Glaucoma from Standard Automated Perimetry", Investigative Ophthalmology & Visual Science, vol. 43, No. 1, Jan. 2002, pp. 162-169.

Goldbaum et al., "Interpretation of Automated Perimetry for Glaucoma by Neural Network", Investigative Ophthalmology & Visual Science, vol. 35, No. 9, Aug. 1994, pp. 3362-3373.

Harwerth et al., "Linking Structure and Function in Glaucoma", Progress in Retinal and Eye Research, 2010, pp. 1-23.

Hood et al., "A Framework for Comparing Structural and Functional Measures of Glaucomatous Damage", Progress in Retinal and Eye Research, vol. 26, 2007, pp. 688-710.

Horn et al., "Continuing Medical Education: Frequency Doubling Technique Perimetry and Spectral Domain Optical Coherence Tomography in Patients with Early Glaucoma", Eye, vol. 25, 2011, pp. 17-29.

Hougaard et al., "Glaucoma Detection by Stratus OCT", J Glaucoma, vol. 16, No. 3, May 2007, pp. 302-306.

(56) References Cited

OTHER PUBLICATIONS

Hougaard et al., "Modeling the Normal Retinal Nerve Fiber Layer Thickness as Measured by Stratus Optical Coherence Tomography", Graefe's Arch Clin. Exp. Ophthalmol, vol. 244, 2006, pp. 1607-1614.

Huang et al., "Development and Comparison of Automated Classifiers for Glaucoma Diagnosis Using Stratus Optical Coherence Tomography", Investigative Ophthalmology & Visual Science, vol. 46, No. 11, Nov. 2005, pp. 4121-4129.

Leitgeb et al., "Ultrahigh Resolution Fourier Domain Optical Coherence Tomography", Optics Express, vol. 12, No. 10, May 17, 2004, pp. 2156-2165.

Leung et al., "Comparative Study of Retinal Nerve Fiber Layer Measurement by StratusOCT and GDx VCC, II: Structure/Function Regression Analysis in Glaucoma", Investigative Ophthalmology & Visual Science, vol. 46, No. 10, Oct. 2005, pp. 3702-3711.

Moller, Martin F., "A Scaled Conjugate Gradient Algorithm for Fast Supervised Learning", PB-339, Nov. 13, 1990, pp. 1-21.

Patel et al., "EEG and MRI Data Fusion for Early Diagnosis of Alzheimer's Disease", 30th Annual International IEEE EMBS Conference, Aug. 20-24, 2008, pp. 1757-1760.

Paunescu et al., "Reproducibility of Nerve Fiber Thickness, Macular Thickness, and Optic Nerve Head Measurements Using StratusOCT", Investigatative Ophthalmology & Visual Science, vol. 45, No. 6, Jun. 2004, pp. 1716-1724.

Poinoosawmy et al., "The Ability of the GDx Nerve Fibre Analyser Neural Network to Diagnose Glaucoma", Graefe's Arch Clin. Exp. Ophthalmol, vol. 239, 2001, 17 pages.

Porter et al., "Three-Dimensional Registration and Fusion of Ultrasound and MRI Using Major Vessels as Fiducial Markers", IEEE Transactions on Medical Imaging, vol. 20, No. 4, Apr. 2001, pp. 354-359.

Racette et al., "Combining Functional and Structural Tests Improves the Diagnostic Accuracy of Relevance Vector Machine Classifiers", J Glaucoma, vol. 19, No. 3, Mar. 2010, pp. 167-175.

Sample et al., "Unsupervised Machine Learning with Independent Component Analysis to Identify Areas of Progression in Glaucomatous Visual Fields", Investigative Ophthalmology & Visual Science, vol. 46, No. 10, Oct. 2005, pp. 3684-3692.

Sato et al., "Correlation Between Retinal Nerve Fibre Layer Thickness and Retinal Sensitivity", Acta Ophthalmologica, vol. 86, 2008, pp. 609-613.

Schuman et al., "Reproducibility of Nerve Fiber Layer Thickness Measurements Using Optical Coherence Tomography", Ophthalmology, vol. 103, No. 11, Nov. 1996, 21 pages.

Sherman et al., "Discordance between Structure and Function in Glaucoma: Possible Anatomical Explanations", Optometry, vol. 80, 2009, pp. 487-501.

Sommer et al., "Clinically Detectable Nerve Fiber Atrophy Precedes the Onset of Glaucomatous Field Loss", Arch Ophthalmol, vol. 109, Jan. 1991, pp. 77-83.

Tucker et al., "A Spatio-Temporal Bayesian Network Classifier for Understanding Visual Field Deterioration", Artificial Intelligence in Medicine, vol. 34, 2005, pp. 163-177.

Turpin et al., "Combining Ganglion Cell Topology and Data of Patients with Glaucoma to Determine a Structure—Function Map", Investigative Ophthalmology & Visual Science, vol. 50, No. 7, Jul. 2009, pp. 3249-3256.

Wald, Lucien, "Some Terms of Reference in Data Fusion", IEEE Transactions on Geoscience and Remote Sensing, vol. 37, No. 3, May 1999, pp. 1190-1193.

Zhu et al., "Predicting Visual Function from the Measurements of Retinal Nerve Fiber Layer Structure", Investigative Ophthalmology & Visual Science, vol. 51, No. 11, Nov. 2010, pp. 5657-5666.

\* cited by examiner

INTEGRATION AND FUSION OF DATA FROM DIAGNOSTIC MEASUREMENTS FOR GLAUCOMA DETECTION AND PROGRESSION ANALYSIS

PRIORITY

This application claims priority to U.S. Provisional Application Ser. No. 61/484,149, filed May 9, 2011, hereby incorporated by reference.

TECHNICAL FIELD

Systems and methods for improving the accuracy of glaucoma diagnosis and progression analysis are presented. In particular one or more aspects of the present invention relate to adjusting the value of an ophthalmic measurement based on information from another type of measurement using a priori knowledge of the relationship between the two measurements. In a preferred embodiment the measurements are from visual field test data and optical coherence tomography test data. Embodiments in which these fused parameters are used in machine learning classifiers for improved glaucoma diagnosis and progression analysis are presented.

BACKGROUND

Glaucoma is an optic neuropathy resulting in characteristic visual field defects. It arises from progressive damage to the optic nerve (ON) and retinal ganglion cells (RGCs) and their axons, the retinal nerve fiber layer (RNFL). Investigating the relationship between development of functional damage in the visual field and structural glaucomatous changes of the RNFL has been the purpose of numerous studies [1-5].

Diagnostic instruments providing quantitative analyses in glaucoma assess either structural or functional aspects of the disease. Optical Coherence Tomography (OCT) is one technique capable of imaging the retina and providing quantitative analysis of RNFL measurements and measuring the optic nerve head. OCT is a noninvasive interferometric technique that provides cross sectional images and thickness measurements of the RNFL (RNFLT) with high resolution [6] and good reproducibility [7-9]. Standard Automated white-on-white Preemptory (SAP) is the standard for assessing visual function by examination of the visual field. Parametric tests are able to provide quantitative measurements of differential light sensitivity at many test point locations in the visual field, and commercially available statistical analysis packages help clinicians in identifying significant visual field loss [10]. The diagnostic performance of both OCT and SAP in glaucoma as well as the correlation between SAP and OCT measurements has been investigated [11-14].

Clinical studies suggest that these diagnostic tests, used in isolation, provide useful information on the diagnosis and progression of the disease and, used in conjunction, provide supportive and complementing information which could lead to improved accuracy in disease detection and monitoring of progression. However, there is not one single diagnostic test used in isolation that provides adequate diagnostic accuracy and applicability across patient populations and disease dynamic range. Multi-modality testing is desired to improve applicability and accuracy. In practice, clinicians are often expected to correlate results from different tests to make a clinical assessment regarding diagnosis and/or progression, usually, based on subjective visual review of multiple reports. Such a task is difficult and subjective, and highly variable across observers.

It is conceivable that integration of functional and structural test measurements could provide more relevant information and thus improved diagnostic performance for classification systems when used as input data. The relevance of integrated diagnostic information is dependent on the underlying relationship between structural and functional measurements. Statistical approaches such as the linear model constructed by Hood et al related RNFLT values to sensitivity losses in SAP [15]. Other studies trying to map the individual visual field test points in SAP to areas of the peripapillary RNFL through different models, showed moderate correlations between visual field sensitivity values and structural measurements [16,17]. More recent attempts to model the function—structure relationship in glaucoma demonstrated that machine learning algorithms, such as radial basis function artificial neural networks (ANNs), improved the modeling accuracy compared to linear methods [18]. Recently Boland et al proposed a structure function index (SFI) as a model to unify retinal ganglion cell structure and function based on knowledge of retinal nerve fiber layer anatomy [41]. The SFI function is the multiplication of 3 probabilities: the probability of disease at a point in the visual field with the probability of abnormality on HRT (Heidelberg Retina Tomograph, Heidelberg Engineering, a confocal scanning laser opthalmoscope that generates and analyzes topographic images of the retina) sector and the probability that these measurements are correlated. These probabilities were derived from glaucoma suspects and not a normal population.

The use of machine learning classifiers (MLCs) in glaucoma diagnosis using either functional or structural measures has been previously explored [19]. MLCs like ANNs have been used for classification of tests based on structural or functional measurements [20-27] and for detection of glaucoma progression [28,29]. ANN-based classification demonstrated better accuracy than linear methods [22, 23, 30] and performed at least as well as human experts [31].

A few studies have examined the diagnostic performance of combining functional and structural data with MLCs for glaucoma diagnosis [32, 33]. One of the main advantages of MLCs is their ability to learn a classification task by training on given examples. Such adaptive classification based on the available data is useful, since a complete analytic theory of the structure-function relationship in glaucoma does not yet exist. The performance of MLCs can be influenced by a number of factors including data selection bias, choice of input and classifier architecture.

In light of the above, there is a need for improved systems and methods for diagnosing and analyzing the progression of glaucoma based on the combination of data from structural and functional measurements and machine learning classification.

SUMMARY

The invention described herein includes novel approaches for modifying or fusing ophthalmic measurement data by utilizing a priori knowledge about the physiologic relationship between the RNFL and visual function in glaucoma to improve the accuracy of individual diagnostic measurements from one type of measurement based on another. This fusing of data can provide improved value to clinicians on its own, in comparison to normative data, or can be used as input data used to train a machine learning classifier network, as well as to affect classifier decisions.

The information fusion framework is an appropriate approach for the analysis of data derived from functional and structural glaucoma diagnostic tests where each test measures different aspects of glaucomatous changes. The fusion method described herein includes the merging of information at the basic data level (data fusion), and is extended to encompass fusion of information at the level of classifiers (decision fusion).

The á priori knowledge that the fusion of SAP visual field measurements and OCT RNFLT data can be based on include but is not limited to:

A model of the anatomical relationship between RNFL morphology and areas of the visual field.

Knowledge of the different data distributions for each type of test. These differences relate to factors such as measurement variability, sources of measurement errors and normative limits for each test. The knowledge may relate to differences that depend on the location of the measurement, the presence and severity of pathology, or knowledge of the natural history of the disease (i.e. structural damage often preceding functional damage).

Statistical processing of the data in relation to the anatomical model and the different data distributions of each test.

This knowledge-based approach enables the merging of test measurements in a specific, non-symmetrical way. As an example, incorporating OCT information with the SAP data can have the effect of either emphasizing or deemphasizing any detected visual field defects, whereas the merging information from SAP to the OCT data can only decrease the measured RNFL thickness depending on the existence of anatomically corresponding visual field defects.

The incorporation of a rule-based/deterministic model into the analyses has advantages compared to other stochastic methods (e.g. to rely on machine learning algorithms only), due to the limited amount of available test data and also due to the transparency of rule-based/deterministic models.

Apart from the fusion of SAP and OCT information at the basic data level, classification systems could also utilize the fusion of decisions from classifiers trained on different sets of fused data. Decision fusion approaches can span from the training of multi-level MLCs (Classification decisions of (first level) MLCs trained on different types of fused data are themselves fused by another (second level) MLC) to other hybrid-MLC approaches (e.g. knowledge-based decision fusion ensembles).

The data fusion could be accomplished in a processor residing in an instrument capable of collecting one or both of the measurement data sets or could be a processor in an analysis workstation (i.e. personal computer) with specialized software that imports the various measurement data sets from data acquisition instruments or over a network.

DETAILED DESCRIPTION

The preferred embodiment of the present invention relates to data fusion of OCT and SAP data. The fused data can be used in Artificial Neural Networks, or other types of machine learning classifiers as will be described in detail below. It should be obvious to one skilled in the art that additional embodiments incorporating the concepts of data fusion between various types of OCT and visual field data and using other types of machine learning classifiers would also fall under the scope of the invention.

OCT Measurements

OCT is a non-invasive, in-vivo imaging technique that is based on the back-scatter or reflectivity of light in a medium. OCT is particularly valuable in ophthalmic examinations, where the beam of light produced by the OCT device scans the eye through the pupil and the image formation process records the back-scattering profile of the light at each location. The intensity of the back-scattered light is indicative of the scattering properties of the tissue and tissue boundaries, and a grayscale cross-sectional image is formed as the light beam sweeps across the field of view (FOV). OCT imaging has dramatically advanced ophthalmic diagnostic capabilities and led also to better understanding of ocular anatomy. It is an established basis of routine ophthalmic practice.

Figure 1:
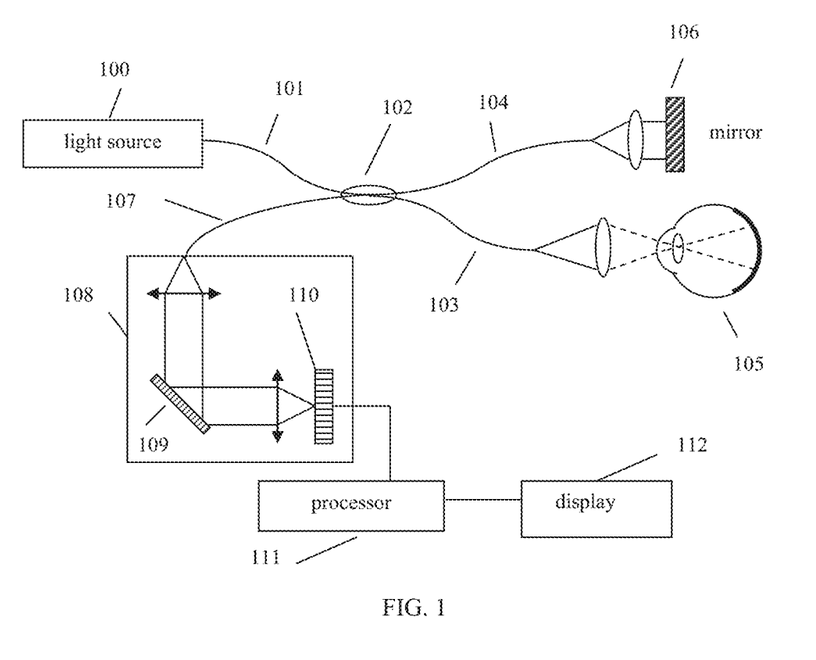
FIG. 1 is a block diagram of a spectral-domain optical-coherence tomography system.

Several implementations of OCT have been developed including time domain (TD-OCT) and frequency domain (spectral domain (SD-OCT) and swept-source (SS-OCT)). FIG. 1 shows a basic block diagram for a spectrometer based SD-OCT system. The light source 100 provides broad bandwidth light to a short length of an optical fiber 101 to an input port of a fiber optic coupler 102, which splits the incoming light beam into the two arms of an interferometer. The two arms each have a section of optical fiber 103 and 104 that guides the split light beam from the fiber coupler 102 to the eye of a patient 105 and a reference reflector 106 respectively. For both the sample arm and the reference arm, at the terminating portion of each fiber, there may be a module containing optical elements to collimate or focus or scan the beam. The returned light waves from the sample 105 and the reference reflector 106 are directed back through the same optical path of the sample and reference arms and are combined in fiber coupler 102. A portion of the combined light beam is directed through a section of optical fiber 107 from the fiber coupler 102 to a spectrometer 108. Inside the spectrometer, the light beam is dispersed by a grating 109 and focused onto a detector array 110. The collected data is sent to a processor 111 and the resulting processed data can be displayed on a display 112 or stored in memory for future reference and processing. Although the system of FIG. 1 includes a reflective reference arm, those skilled in the art will understand that a transmissive reference arm could be used in its place.

The interference between the returned light waves from the sample and reference arms causes the intensity of the combined light to vary across the spectrum. The Fourier transform of the interference spectrum reveals the profile of scattering intensities at different path lengths, and therefore scattering as a function of depth in the sample (see for example Leitgeb et al., "Ultrahigh resolution Fourier domain optical coherence tomography," Optics Express 12(10):2156 2004). The profile of scattering as a function of depth is called an axial scan (A-scan or A-line). A set of A-scans measured at neighboring locations in the sample produces a cross-sectional image (tomogram or B-scan) of the sample. Note that the principle of operation of a tunable laser based swept source OCT is very similar to that of a spectrometer based spectral domain OCT system (see for example, Choma et al. "Sensitivity advantage of swept source and Fourier domain optical coherence tomography." *Optics Express* 11(18): 2183-2189 2003), hence the spectral domain OCT system for obtaining the OCT measurement data can also be a swept source OCT system or any type of imaging system that provides visualization of the retinal layers in three dimensions.

One commercially available SD-OCT system is the Cirrus HD-OCT (Carl Zeiss Meditec, Inc. Dublin, Calif.). Several of the measurements provided by this system could be used in the fusion techniques of the present invention. Standard RNFLT parameters provided in the analysis printout include average thickness measurements for the whole scan circle, the four quadrants and the 12 clock hour sectors of each scan, while highlighting the values that fall below the 5% and 1% significance level, based on comparison to the instrument's normative database. Averaged A-scan values can be decreased in complexity by means of principal component analysis (PCA) to maintain 99.9% of the variation in the data, into 22 parameters. In another embodiment, RNFLT data can be corrected for age and refractive status (spherical equivalent) based on normative databases. The use of A-scan derived parameters as input in automated classifiers has been addressed previously [24].

SAP Measurements

Figure 2:
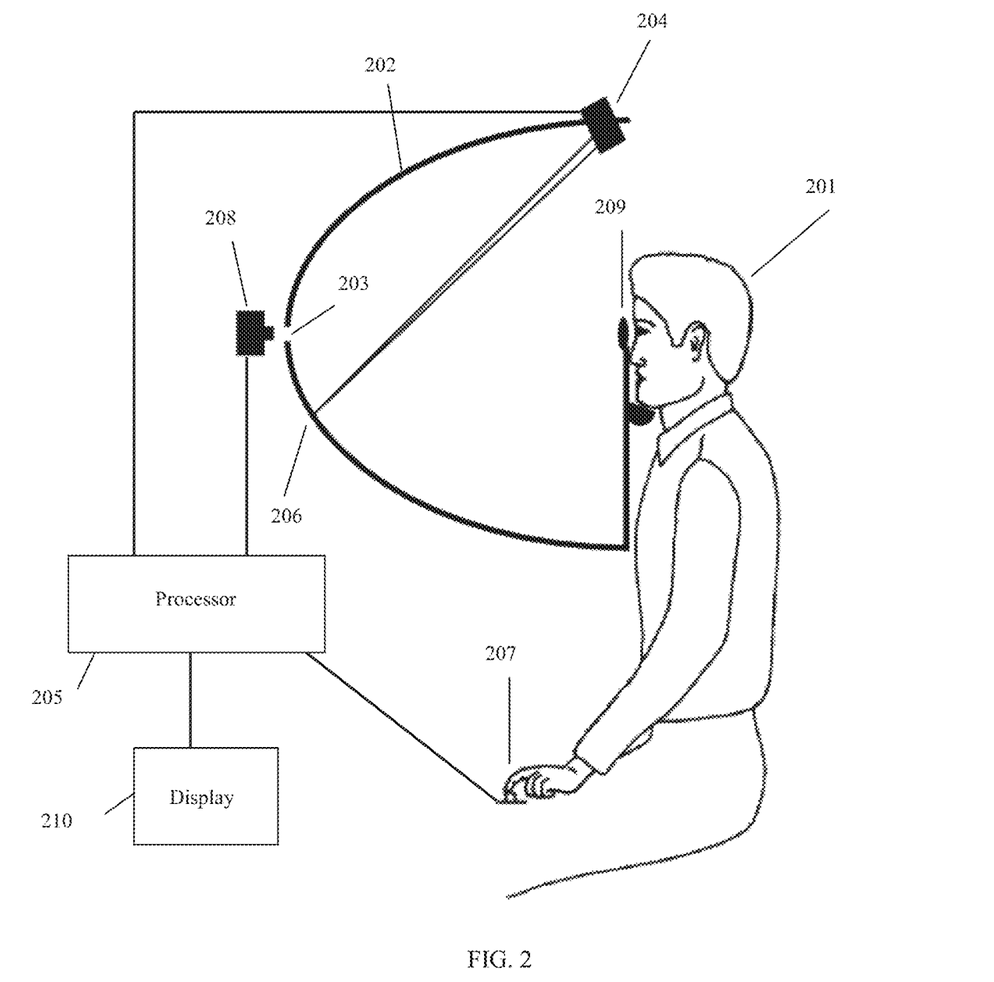
FIG. 2 is a block diagram of a visual field analyzer.

The Humphrey HFA (Carl Zeiss Meditec, Inc. Dublin, Calif.), is one type of standard automated perimeter that can be used to provide SAP data for the present invention. A block diagram of a field analyzer is illustrated in FIG. 2. A patient 201 is shown observing a hemispherical projection screen 202. The patient is instructed to fixate at a point at the center of the hemispherical screen 203. A projector 204 under control of a processor 205 projects a series of spots 206 onto the screen. The patient indicates that the spot 206 of light was seen by depressing button 207. The response is recorded by the processor 205. A camera 208 can be used to monitor the gaze of the patient throughout the test. The images from the gaze camera can optionally be displayed (on display 210) to the clinician for aid in patient alignment or test verification. A trial lens holder 209 is positioned in front of the eye of the patient being tested to correct the refractive error of the patient. The point of projection on the hemispherical projection screen controllably changes to positions spaced apart from the fixation light source. Preferably, the point is varied in intensity as the point moves from position to position on the hemispherical projection screen. By positioning the point to known locations on the hemispherical projection screen and changing the brightness (in a total amount of about four decades), the sensitivity of the patient's retina is measured and mapped. While FIG. 2 shows a projection type visual field tester, the subject invention can be used with other types of testers, including those that generate images through LCD or other displays. (See for example U.S. Pat. No. 8,132,916 hereby incorporated by reference). A visual field map can be constructed using various analysis algorithms such as the Swedish Interactive threshold algorithm (SITA, see for example U.S. Pat. Nos. 5,461,435, 5,381,195, and 5,598,235)

The HFA device is capable of providing several different measurements. The Glaucoma Hemifield Test (GHT) index is available in the standard analysis printout of SAP tests. It is an expert system that classifies SAP tests as within normal limits, borderline or outside normal limits, based on the differences of pattern deviation values between test points in mirror image areas of the upper and lower hemispheres of the visual field. This index can be used as a reference standard to for the specificity and sensitivity of any classifier—any acceptable classifier should improve on this currently available metric. For each SAP test, numerical values based on the pattern deviation probability map can be scored using a probability scale identical to that used in calculating the GHT [36]. The performance benefits of using pattern deviation probability scores as input to ANNs has been previously described [20].

Data Fusion

Figure 3:
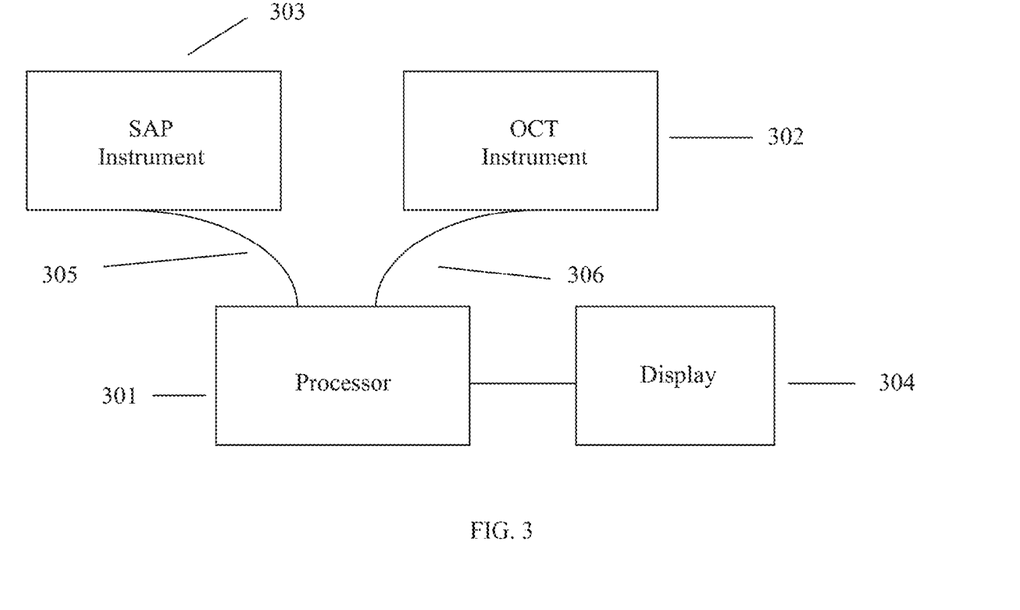
FIG. 3 illustrates one embodiment of the invention in which a separate processor connected to OCT and SAP instruments carries out the data fusion of the present invention.
Figure 4:
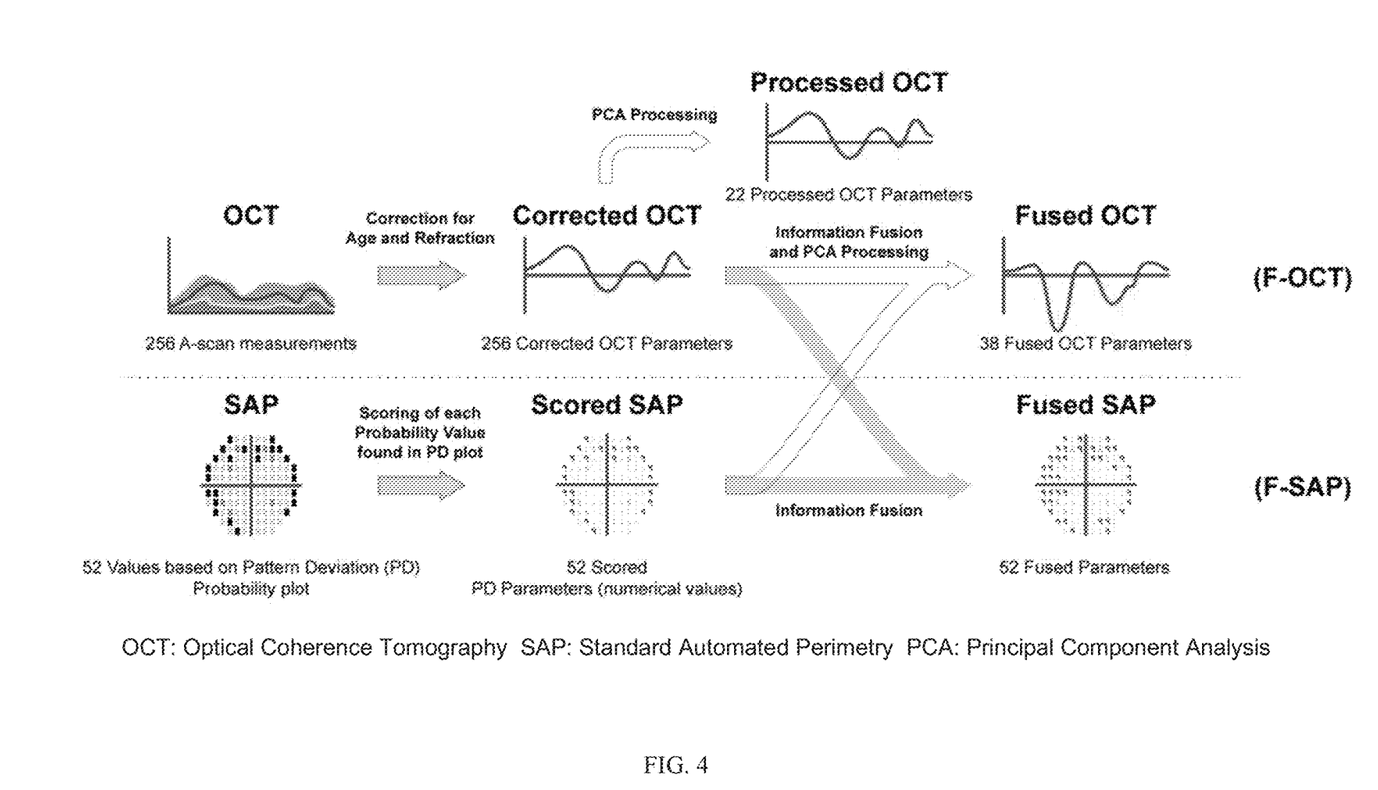
FIG. 4 illustrates an embodiment of the present invention in which OCT and SAP data are fused based on the other modality.

The Cirrus and HFA devices are just two examples of devices capable of collecting the measurement data used in the present invention. It would be obvious to those skilled in the art that many other devices would be capable of collecting data that could be used. The fusion process could be carried out in a processor in either instrument with the other data set being imported for analysis purposes either via a networked connection or through other data transfer methods. Alternatively, as illustrated in FIG. 3, the data fusion could be carried out on a separate processor 301 located for example in an analysis workstation, where the processor is connected to an OCT instrument 302 and a standard automated perimeter 303, and data is received by the processor, preferably over networked connections 305 and 306, prior to analysis. The analysis workstation could be in the same location as the instruments or in a remote location. The results of the analysis are displayed to the user on display 304.

FIG. 3 illustrates the steps involved with fusing OCT data with SAP data and vice versa based on one embodiment of the present invention. The steps in this embodiment include:

1) Adjusting one or both datasets to account for known sources of additional variability in comparison to normal values, including age and refractive error.
2) Transforming one or both datasets using a statistical model adapted to the dataset (i.e. principal component analysis) to identify a subset of the data to use. Alternatively, a scoring method may be used to identify the subset of interest.
3) Creating a fused dataset by adjusting the data from one transformed data set according to information from the other transformed dataset. This may use knowledge of the anatomical relationship between the two datasets.
4) Presenting the fused data for review by the clinician, or using it as the input to a machine learning classifier. Alternatively, the data could be presented after comparing it to similarly processed normative data, or after following it over multiple visits to identify progressive damage.

Detailed descriptions of fused OCT and SAP parameters will be discussed in detail below. While the discussion here is focused on fusing OCT data using SAP data and vice versa, the methods could equally apply to fusing of different types of measurements made from a single instrument. An example of using two OCT measurements as the input to create a fused final set of OCT measurements might include using a macular measurement of the inner retinal thickness to modify RNFL measurements in the presence of papilledema or other optic nerve head swelling. In this case, the a priori knowledge that the observed RNFL measurements are impacted by edematous swelling can be counteracted by reducing the observed RNFL measurement to match the unaffected ganglion cell layer thickness in anatomically related locations.

Fused OCT parameters

One method for creating fused OCT parameters using RNFL measurements as the OCT dataset and SAP measurements as the functional dataset would use anatomical relationships known in the literature as well as statistical modifications adapted to the particular measurements. The map constructed by Garway-Heath et al [35] to represent the relationship between RNFLT of OCT scan circle sectors and differential light sensitivity in specific areas of the visual field can be used to divide the OCT scan circle and the SITA standard 24-2 SAP test points into 6 sectors accordingly. The probability values for each age- and refraction corrected OCT A-scan measurement and sectoral measurement of our test dataset, can then be calculated. A-scan values falling below the fifth percentile of the distribution in normal reference material can be transformed through multiplication with an exponential factor. In this embodiment, this factor is constructed by calculating the average pattern deviation probability scores (i.e. the sum of all pattern deviation scores divided by the number of SAP test points) of the visual field sector corresponding to each of the OCT scan circle sectors. The fused A-scan values then depend on the decrease in RNFLT for the specific A-scan position relative to the distribution of the normative reference material, and the status of the visual field sector corresponding to that location. These fused measurements can be displayed to the user (i.e. in a TSNIT thickness profile of the RNFL) or be used as input in a machine learning classifier as will be described in detail below.

Fused SAP Parameters

The same anatomical relationship can be used in the formation of a fused SAP dataset using SAP as the functional input and OCT RNFL measurements to adjust them. Given the decibel nature of the SAP data, an additive model is preferred to the multiplicative model used above. Where the structural measurements could only be reduced by comparison to functional measurements, the fused functional measurement could be adjusted up or down.

As with the OCT scan circle values, SITA standard 24-2 SAP test points can be divided into six sectors based on the map by Garway-Heath et al [35]. For every visual field sector, the pattern deviation probability score at each test point can be transformed by an additive factor. In this embodiment, this factor is derived from the corrected A-scan measurements of the corresponding OCT sector. All A-scan measurements are identified in each OCT sector, and their probability values assigned a score according to significance level of the deviation from the values of a normative database. In this embodiment, the probability scoring scale is similar to that used in the calculation of the GHT [36]. Here, the scored probability value from each OCT sector (i.e. the lowest scored probability below the fifth percentile or the highest scored probability above the ninety-fifth percentile of our normal RNFLT distribution) is used as a factor in the fusion process. The fused SAP parameters are obtained by adding this factor to the SAP pattern deviation probability score of each SAP test point in the corresponding visual field sector. In the event that both high and low scored probability values (outside the fifth or ninety-fifth percentile of our normative RNFLT database) existed in the same OCT sector, only the low value is used in the summation process. The fused SAP measurements thus depend on both the status of the visual field sector reflected by the pattern deviation probability scores, and the thickness of the corresponding OCT sector. Visual field defects as indicated by the pattern deviation probability scores could be either accentuated or attenuated during the fusion procedure, depending on the factor of scored probability from the corresponding OCT sector. The adjusted parameters can be displayed on a visual field map or be used as input in machine learning classification.

Machine Learning Classification

Machine Learning can be defined as the scientific approach or process concerned with the construction and deployment of algorithms that exhibit an adaptation of their function/structure based on data that is presented to them during a learning process. Machine learning algorithms can discover patterns of interest or relationships in the underlying unknown distributions of the data that is presented, and then generalize their decision functions to new, previously unseen, data. Machine learning algorithms can perform both regression and classification tasks.

Classification tasks include both binary (2 class) classification, and multi-class classification. During the learning process, Machine Learning Classifiers (MLCs) adaptively change the decision boundary that separates the classes of objects to be classified according to an error measure. By minimizing this error function MLCs attempt to optimize the separation of the classes.

The types of MLCs can be categorized based on the type of learning process and the algorithmic architectural characteristics. In Supervised learning inputs are mapped to desired outputs based on training examples (targets) of known class). Algorithms (including both discriminative and generative classifiers) belonging to this class:
  Types of Artificial Neural Networks (ANNs) like the Multi Layer Perception, Radial Basis Function (network) classifiers, Learning Vector Quantization
  Methods based on statistical learning theory like Support Vector Machines (SVMs) and their variants (e.g. least square support vector machines) as well as the probabilistic variant of SVMs, Relevance Vector Machines.
  Methods based on Bayesian statistics ranging from the simple naïve bayes classifier to the more complex bayesian neural networks
  Boosting and Bagging classifiers
  Decision tree algorithms and variants such as random forest algorithms
  Kernel estimators (a special case of this is k-nearest neighbor (lazy learning algorithm))
  Markov networks, Hidden Markov Models, Markov Decision Process
  Mixture models (Gaussian Mixture Models)
  Committee Machines (types include Ensemble methods, mixture of experts and hierarchical mixture of experts)
  Restricted Boltzman machines
  Linear discriminant functions
  Quadratic classifiers (quadratic discriminant analysis)
  Transductive Support Vector Machines (transductive learning algorithm)
  Information Fuzzy Networks
  Q-learning algorithm, a type of reinforcement learning algorithm (and variations of it, like the delayed Q-learning algorithm)
  Probably Approximately Correct (PAC) learning algorithm
  Unsupervised learning involves modeling the distribution of sets of inputs. These algorithms are mainly used in clustering of data. Algorithms belonging to this class include:
  Kohonen networks (self-organizing maps)
  Generative Topographic Map
  Vector Quandization
  Mixture models
  Expectation-maximization algorithm
  Adaptive Resonance Theory (ART) models
  Independent Component Analysis The above list is of course not all-inclusive, but refers to the main types of algorithms in machine learning. Other approaches combining machine learning with methods from fuzzy logic, dynamic programming, evolutionary computation and combinatorial optimization, are also possible.

While the methods described herein relate to SAP and specific OCT measurements, the concepts would apply equally to other types of visual field and OCT measurement data.

In a preferred embodiment, the ANNs are trained and tested using the perimetric pattern deviation probability scores and the age- and refraction corrected OCT A-scan measurements after PCA preprocessing, as well as the fused SAP and OCT parameters. Integration of the above parameters may also be achieved by simply combining them. Classification may be achieved by integrating non-fused SAP and OCT parameters, fused OCT and SAP parameters or a combination of the two.

Artificial Neural Networks (ANN)

In this embodiment, the ANN classifier consisted of an ensemble of thirty-five fully connected cascade-forward Multi Layer Perceptrons (MLPs). The architecture of the ANNs (number of hidden layers and neurons) can be optimized depending on the type of input used in order to achieve the best performance as judged by the results derived from any validation procedure, including a 10-fold cross validation procedure. In this embodiment, ANNs were constructed with the MATLAB neural network toolbox version 7 (The MathWorks Inc, Natick, Mass., USA) and trained with the scaled conjugate gradient algorithm [37].

ANNs were trained and tested with the 10-fold cross-validation procedure, to reduce bias from training and testing on the same individuals, while fully utilizing our data set. Data were randomly divided into ten subsets, each containing test data from an approximately equal proportion of glaucoma patients and healthy individuals. One subset was used to test classification performance while the remaining nine subsets were used for training purposes. In our ANN ensemble, one out of the nine training subsets was reserved for early stopping of the ANNs in order to avoid overfitting. We additionally used bagging [38] of the remaining eight subsets to create the training sets used by the ANN ensemble. During training, this process was iterated, each time using a different subset as the early stopping set, until all the data subsets had been used to both train and stop the training of the ensemble. We further iterated the training process using each time a different test subset, so that all data could be used both for training and testing the classifiers, and averaged the test results in order to produce a single performance measure for each ANN.

Analyses

In any implementation of a classifier, it is important to measure the classification. This is typically done by calculating the area under the ROC curve (AROC). Integration of fused data should offer higher diagnostic accuracy compared to the best performing SAP and OCT algorithms that exist in the available analysis packages of each instrument.

The combination of structural and functional information contained in the OCT and SAP test data respectively, can be viewed as a type of information integration. The simplest way to integrate the different types of data is to construct a vector that consists of all OCT and SAP measurements. As described above, alternate embodiments include novel input parameters that fuse both structural and functional measurements. Integrating information about the structure-function relationship of glaucomatous damage through data fusion, presents some advantages over the simple combination of the two different types of data. Instead of relying on MLCs to learn about the structure-function relationship based on limited training data, the fusion process allows for direct incorporation of prior knowledge obtained in other independent large datasets about the topographic relationship between structural and functional measurements into the classification problem. Controlling the incorporation of knowledge into MLCs can also counteract the lack of insight on the way stochastic processes like ANNs represent and use the acquired knowledge in their classification decisions. These classifiers have been shown to be more robust since the likelihood of a false positive or false negative test result by both fused OCT and SAP based ANNs was significantly lower (Bizios et al. "Integration and fusion of standard automated perimetry and optical coherence tomography data for improved automated glaucoma diagnostics" BMC Ophthalmology 2011 11:20). Such improvements in performance need not be specific to the ANN's described above, but could be also seen with another MLC, a relevance vector machine (RVM) classifier.

The embodiment described above represents the structure-function relationship of the SAP and OCT measurements based on the previously published topographic map by Garway-Heath et al [35]. Other mappings including one type of OCT data with another type of OCT data could also be considered. For instance, a particular location around the optic nerve head could be mapped to an anatomically related location on the measurement circle for the RNFL. This mapping could be used to allow measurements of the neuroretinal rim around the optic disc to 'fuse' or modify measurements of the RNFL or vice versa. This might be most usefully done in early disease when the ONH measurements may be compromised by blood vessels that occupy the optic disc and are difficult to distinguish from genuine neuroretinal tissue. Alternately, measurements of the ganglion cell layer in the macular area may be less affected by floor effects than the peripapillary measurements. Thus they may usefully modify the RNFL measurements in late stage disease. In each of these cases the process of fusion would allow a more complete picture of the true state of disease than might be possible by a single measurement of representative tissue which is limited in one way or another.

The use of principal component analysis for dimensionality reduction of the OCT and fused OCT data could be replaced with a non-linear dimensionality reduction algorithm, which might provide better representations of complex data, although their extensions to new data are iterative in nature without exact numerical solutions in most cases.

The bias in selecting a structure- or function-related reference standard, affects the accuracy of combinatorial analyses by erroneous estimations of specificity, sensitivity and correlation measures of the examined structural and functional parameters. One possible reference standard could be based on clinical examination of ONH morphology. Other reference standards could be considered.

The significant differences in age and refraction between healthy individuals and glaucoma patients are accounted for both in the pattern deviation probability based SAP input and the age- and refraction-corrected OCT input.

The incorporation of knowledge about known rules into black box classifiers could enable the construction of ANN-based systems that are more closely related to grey box models (i.e. models with known general structure but also unknown parameters), allowing for greater insight into the classification process and more effective sensitivity analyses of the test input parameters. Such advantages could facilitate the practical deployment of ANNs as decision support systems in glaucoma diagnostics.

The combination and fusion of data from OCT and SAP has the potential to increase the accuracy of glaucoma diagnostics compared to parameters from either instrument alone. Moreover, fusion of test measurements could lead to test parameters that better reflect both the structural and functional glaucomatous changes that occur during the course of the disease, providing more relevant information to glaucoma diagnostic systems.

Although various embodiments that incorporate the teachings of the present invention have been shown and described in detail herein, those skilled in the art can readily devise many other varied embodiments that still incorporate these teachings.

The following references are hereby incorporated by reference:

1. Ajtony C, Balla Z, Somoskeoy S, Kovacs B: Relationship between Visual Field Sensitivity and Retinal Nerve Fiber Layer Thickness as Measured by Optical Coherence Tomography. *Investigative Ophthalmology & Visual Science* 2007, 48(1):258-263.
2. Sommer A, Katz J, Quigley H A, Miller N R, Robin A L, Richter R C, Witt K A: Clinically detectable nerve fiber atrophy precedes the onset of glaucomatous field loss. *Arch Ophthalmol* 1991, 109(1):77-83.
3. Sato S, Hirooka K, Baba T, Yano I, Shiraga F: Correlation between retinal nerve fibre layer thickness and retinal sensitivity. *Acta Ophthalmologica* 2008, 86(6):609-613.
4. Harwerth R S, Wheat J L, Fredette M J, Anderson DR: Linking structure and function in glaucoma. *Progress in retinal and eye research* 2010, 29(4):249-271.
5. Gardiner S K, Johnson C A, Cioffi G A: Evaluation of the Structure-Function Relationship in Glaucoma. *Investigative Ophthalmology & Visual Science* 2005, 46(10):3712-3717.
6. Chang R, Budenz D L: New developments in optical coherence tomography for glaucoma. *Curr Opin Ophthalmol* 2008, 19(2):127-135.
7. Schuman J S, Pedut-Kloizman T, Hertzmark E, Hee M R, Wilkins J R, Coker J G, Puliafito C A, Fujimoto J G, Swanson E A: Reproducibility of nerve fiber layer thickness measurements using optical coherence tomography. *Ophthalmology* 1996, 103(11):1889-1898.
8. Paunescu L A, Schuman J S, Price L L, Stark P C, Beaton S, Ishikawa H, Wollstein G, Fujimoto J G: Reproducibility of nerve fiber thickness, macular thickness, and optic nerve head measurements using StratusOCT. *Invest Ophthalmol Vis Sci* 2004, 45(6):1716-1724.
9. Budenz D L, Chang R T, Huang X, Knighton R W, Tielsch J M: Reproducibility of retinal nerve fiber thickness measurements using the stratus OCT in normal and glaucomatous eyes. *Invest Ophthalmol Vis Sci* 2005, 46(7):2440-2443.
10. Bengtsson B, Olsson J, Heijl A, Rootzén H: A new generation of algorithms for computerized threshold perimetry, SITA. *Acta Ophthalmologica Scandinavia* 1997, 75(4):368-375.
11. Budenz D L, Michael A, Chang R T, McSoley J, Katz J: Sensitivity and specificity of the StratusOCT for perimetric glaucoma. *Ophthalmology* 2005, 112(1):3-9.
12. Hougaard J L, Heijl A, Bengtsson B: Glaucoma detection by Stratus OCT. *J Glaucoma* 2007, 16(3):302-306.
13. Leung C K, Chong K K, Chan W M, Yiu C K, Tso M Y, Woo J, Tsang M K, Tse K K, Yung W H: Comparative study of retinal nerve fiber layer measurement by StratusOCT and GDx VCC, II: structure/function regression analysis in glaucoma. *Invest Ophthalmol Vis Sci* 2005, 46(10):3702-3711.
14. El Beltagi T A, Bowd C, Boden C, Amini P, Sample P A, Zangwill L M, Weinreb R N: Retinal nerve fiber layer thickness measured with optical coherence tomography is related to visual function in glaucomatous eyes. *Ophthalmology* 2003, 110(11):2185-2191.
15. Hood D C, Kardon R H: A framework for comparing structural and functional measures of glaucomatous damage. *Progress in retinal and eye research* 2007, 26(6):688-710.
16. Ferreras A, Pablo L E, Garway-Heath D F, Fogagnolo P, García-Feijoo J: Mapping standard automated perimetry to the peripapillary retinal nerve fiber layer in glaucoma. *Investigative ophthalmology & visual science* 2008, 49(7):3018-3018.
17. Turpin A, Sampson G P, McKendrick A M: Combining Ganglion Cell Topology and Data of Patients with Glaucoma to Determine a Structure-Function Map. *Investigative Ophthalmology & Visual Science* 2009, 50(7):3249-3256.
18. Zhu H, Crabb D P, Schlottmann P G, Lemij H G, Reus N J, Healey P R, Mitchell P, Ho T, Garway-Heath D F: Predicting Visual Function from the Measurements of Retinal Nerve Fiber Layer Structure. *Investigative Ophthalmology & Visual Science* 2010, 51(11):5657-5666.
19. Bowd C, Goldbaum M H: Machine learning classifiers in glaucoma. *Optometry & Vision Science* 2008, 85(6):396-396.
20. Bengtsson B, Bizios D, Heijl A: Effects of input data on the performance of a neural network in distinguishing normal and glaucomatous visual fields. *Invest Ophthalmol Vis Sci* 2005, 46(10):3730-3736.
21. Bizios D, Heijl A, Bengtsson B: Trained artificial neural network for glaucoma diagnosis using visual field data: a comparison with conventional algorithms. *J Glaucoma* 2007, 16(1):20-28.
22. Chan K, Lee T W, Sample P A, Goldbaum M H, Weinreb R N, Sejnowski T J: Comparison of machine learning and traditional classifiers in glaucoma diagnosis. *IEEE Trans Biomed Eng* 2002, 49(9):963-974.
23. Goldbaum M H, Sample P A, Chan K, Williams J, Lee T W, Blumenthal E, Girkin C A, Zangwill L M, Bowd C, Sejnowski T et al: Comparing machine learning classifiers for diagnosing glaucoma from standard automated perimetry. *Invest Ophthalmol Vis Sci* 2002, 43(1):162-169.
24. Bizios D, Heijl A, Hougaard J L, Bengtsson B: Machine learning classifiers for glaucoma diagnosis based on classification of retinal nerve fibre layer thickness parameters measured by Stratus OCT. *Acta Ophthalmologica* 2010, 88(1):44-52.
25. Burgansky-Eliash Z, Wollstein G, Chu T, Ramsey J D, Glymour C, Noecker R J, Ishikawa H, Schuman J S: Optical coherence tomography machine learning classifiers for glaucoma detection: a preliminary study. *Invest Ophthalmol Vis Sci* 2005, 46(11):4147-4152.
26. Huang M L, Chen H Y: Development and comparison of automated classifiers for glaucoma diagnosis using Stratus optical coherence tomography. *Invest Ophthalmol Vis Sci* 2005, 46(11):4121-4129.
27. Poinoosawmy D, Tan J C, Bunce C, Hitchings R A: The ability of the GDx nerve fibre analyser neural network to diagnose glaucoma. *Graefes Arch Clin Exp Ophthalmol* 2001, 239(2):122-127.
28. Sample P A, Boden C, Zhang Z, Pascual J, Lee T W, Zangwill L M, Weinreb R N, Crowston J G, Hoffmann E M, Medeiros F A et al: Unsupervised machine learning with independent component analysis to identify areas of progression in glaucomatous visual fields. *Invest Ophthalmol Vis Sci* 2005, 46(10):3684-3692.
29. Tucker A, Vinciotti V, Liu X, Garway-Heath D: A spatiotemporal Bayesian network classifier for understanding visual field deterioration. *Artif Intell Med* 2005, 34(2):163-177.
30. Bowd C, Chan K, Zangwill L M, Goldbaum M H, Lee T W, Sejnowski T J, Weinreb R N: Comparing neural networks and linear discriminant functions for glaucoma detection using confocal scanning laser ophthalmoscopy of the optic disc. *Invest Ophthalmol Vis Sci* 2002, 43(11):3444-3454.
31. Goldbaum M H, Sample P A, White H, et al. Interpretation of automated perimetry for glaucoma by neural network. *Invest Ophthalmol Vis Sci* 1994, 35:3362-3373.

32. Bowd C, Hao J, Tavares I M, Medeiros F A, Zangwill L M, Lee T W, Sample P A, Weinreb R N, Goldbaum M H: Bayesian machine learning classifiers for combining structural and functional measurements to classify healthy and glaucomatous eyes. *Investigative ophthalmology & visual science* 2008, 49(3):945-945.

33. Racette L, Chiou C Y, Hao J, Bowd C, Goldbaum M H, Zangwill L M, Lee T W, Weinreb RN, Sample P A: Combining functional and structural tests improves the diagnostic accuracy of relevance vector machine classifiers. *Journal of glaucoma* 2010, 19(3):167-167.

34. Hougaard J L, Ostenfeld C, Heijl A, Bengtsson B: Modelling the normal retinal nerve fibre layer thickness as measured by Stratus optical coherence tomography. *Graefes Arch Clin Exp Ophthalmol* 2006, 244(12):1607-1614.

35. Garway-Heath D F, Poinoosawmy D, Fitzke F W, Hitchings R A: Mapping the visual field to the optic disc in normal tension glaucoma eyes. *Ophthalmology* 2000, 107(10):1809-1815.

36. Asman P, Heijl A: Glaucoma Hemifield Test: Automated Visual Field Evaluation. *Archives of Ophthalmology* 1992, 110(6):812-819.

37. Møller M F: A Scaled Conjugate Gradient Algorithm for Fast Supervised Learning. *Neural Networks* 1993, 6:525-533.

38. Haykin S S: Neural networks: a comprehensive foundation, 2nd edn. Upper Saddle River, N.J.: Prentice Hall; 1999.

39. DeLong E R, DeLong D M, Clarke-Pearson D L: Comparing the areas under two or more correlated receiver operating characteristic curves: a nonparametric approach. *Biometrics* 1988, 44(3):837-845.

40. Arthur S N, Aldridge A J, Leon-Ortega J D, McGwin G, Xie A, Girkin C A: Agreement in Assessing Cup-to-Disc Ratio Measurement Among Stereoscopic Optic Nerve Head Photographs, HRT II, and Stratus OCT. *Journal of glaucoma* 2006, 15(3):183-189.

41. Boland M V, Quigley H A: Evaluation of a combined index of optic nerve structure and function for glaucoma diagnosis. *BMC Ophthalmology* 2011, 11(6).

42. Leitgeb et al., "Ultrahigh resolution Fourier domain optical coherence tomography," *Optics Express* 12(10):2156 2004.

43. Choma et al. "Sensitivity advantage of swept source and Fourier domain optical coherence tomography." *Optics Express* 11(18): 2183-2189 2003.

44. US Patent Publication No. 2011/0190657 Zhou et al/"Glaucoma Combinatorial Analysis"

45. U.S. Pat. No. 8,132,916 Johansson et al. "High precision contrast ratio display for visual stimulus"

46. Bizios et al. "Integration and fusion of standard automated perimetry and optical coherence tomography data for improved automated glaucoma diagnostics" BMC Ophthalmology 2011 11:20

47. U.S. Pat. No. 5,381,195 Rootzen et al. "Method and apparatus for testing a subject's perception of visual stimuli 48. U.S. Pat. No. 5,461,435 Rootzen et al. "Method and an apparatus for checking the thresholds of a subject's perception of visual stimuli"

49. U.S. Pat. No. 5,598,235 Heijl et al. "Method and an apparatus for testing a subject's response to visual stimuli"

What is claimed is:

1. A method of improving the accuracy of ophthalmic diagnostic measurements of disease in the eye of a patient, said method comprising:

collecting optical coherence tomography (OCT) measurements of the eye of a patient using an optical coherence tomography device, said OCT measurements corresponding to scattering intensity as a function of depth in the eye;

collecting visual field test measurements on the eye of a patient using a perimetry device;

adjusting the values of a plurality of the measurements made from one of above collection steps based on the measurements from the other collection step and á priori knowledge of the relationship between the two types of measurements, wherein said adjusting step includes one or both of:

(a) transforming the OCT measurements using a mathematical function based on the visual field test measurements obtained from corresponding regions of the eye; or (b) transforming the visual field test measurements using a mathematical function based on the OCT measurement obtained from corresponding regions of the eye; and storing or displaying the adjusted value.

2. A method as recited in claim 1, wherein the adjustment is made only when a measurement falls within a predefined criteria.

3. A method as recited in claim 1, wherein the adjusted value is compared to normative data.

4. A method as recited in claim 1, wherein the adjusted value is used to determine the progression of disease.

5. A method as recited in claim 1, wherein the adjusted parameters are used as input in a machine learning classifier.

6. A method as recited in claim 1, wherein the machine learning classifier is an artificial neural network.

7. A method of facilitating the analysis of disease conditions in the eye of a patient comprising the steps of:

obtaining a set of structural measurements of the eye with an optical coherence tomography (OCT) device, said OCT measurements corresponding to scattering intensity as a function of depth in the eye;

obtaining a set of visual functions measurements with a perimetry device;

modifying the visual function measurements with information from the structural measurements taking into account a priori knowledge about the relationship between the two types of measurements, and wherein said modification includes transforming the visual function measurements using a mathematical function based on the OCT measurement obtained from corresponding regions of the eye; and displaying a perimetry map based upon the modified visual function measurements.

8. A method as recited in claim 7, wherein the modified visual function measurements are classified.

9. A method as recited in claim 8, wherein the classification is based on the level of glaucoma present in the eye.

10. A method as recited in claim 7, wherein the á priori knowledge includes a model of the anatomical relationship between retinal nerve fiber layer (RNFL) morphology and areas of the visual field.

11. A method as recited in claim 7, wherein the á priori knowledge includes information related to difference in data distributions for the OCT and perimetry measurements.

12. A method as recited in claim 11, wherein the differences in data distributions includes one or more of the following factors: measurement variability, sources of measurement errors and normative limits for each measurement.

13. A method as recited in claim 7, wherein the modification of the visual function measurements increase some of the visual field defects and decrease some different visual field defects.

14. A method as recited in claim 7, wherein the perimetry map is in the form of a Glaucoma Hemifield Test.

15. A method as recited in claim 7, further including adjusting the visual function measurements to account for variability caused by age.

16. A method as recited in claim 7, further including adjusting the visual function measurements to account for variability caused by refractive error.

17. A method as recited in claim 7, further including adjusting the structural measurements to account for variability caused by age.

18. A method as recited in claim 7, further including adjusting the structural measurements to account for variability caused by refractive error.

19. A method as recited in claim 7, further including transforming the structural measurements using a statistical model to identify a subset of measurements used to modify the visual function measurements.

20. A method as recited in claim 7, further including transforming the visual function measurements using a statistical model to identify a subset of measurements that are modified by the structural measurements.

21. A system for analyzing the disease condition of an eye of a patient said system comprising:
a processor for receiving a set of structural measurements of the eye collected with an optical coherence tomography (OCT) device, said OCT measurements corresponding to scattering intensity as a function of depth in the eye and receiving a set of visual function measurements collected with a perimetry device, said processor adjusting the values of a plurality of the measurements made from one of the two data sets based on the measurements from the other data set and a priori knowledge of the relationship between the two types of measurements, and wherein the adjustment of the values include one or both of:
(a) transforming the OCT measurements using a mathematical function based on the visual function measurements obtained from corresponding regions of the eye; or
(b) transforming the visual function measurements using a mathematical function based on the OCT measurement obtained from corresponding regions of the eye; and
a display for displaying one or more adjusted measurement values.

22. A system as recited in claim 21, wherein the adjustment is made only when a measurement falls within a predefined criteria.

23. A system as recited in claim 21, wherein the adjusted value is compared to normative data.

24. A system as recited in claim 21, wherein the adjusted parameters are used as input in a machine learning classifier.

25. A system as recited in claim 21, wherein the machine learning classifier is an artificial neural network.

26. The method as recited in claim 1, wherein the values of the plurality of the measurements are adjusted based on a priori knowledge of the severity of the disease in the eye of the patient.

27. The method as recited in claim 7, wherein visual function measurements are modifying based on a priori knowledge of the severity of the disease in the eye of the patient.

28. A system as recited in claim 21, wherein the values of the plurality of the measurements are adjusted based on a priori knowledge of the severity of the disease in the eye of the patient.

29. A system as recited in claim 21, wherein the adjusted values is used to determine the progression of disease.

* * * * *